United States Patent
Braido et al.

(10) Patent No.: US 10,639,148 B2
(45) Date of Patent: May 5, 2020

(54) METHOD OF PLACING A PROSTHETIC VALVE ASSEMBLY IN A PATIENT'S CIRCULATORY SYSTEM

(71) Applicant: St. Jude Medical, Cardiology Division, Inc., St. Paul, MN (US)

(72) Inventors: Peter N. Braido, Wyoming, MN (US); Gary W. Geiger, Fridley, MN (US); Thomas Mark Benson, Minneapolis, MN (US); Steven Frederick Anderl, Forest Lake, MN (US); Aditee Kurane, Oakdale, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 141 days.

(21) Appl. No.: 15/659,020

(22) Filed: Jul. 25, 2017

(65) Prior Publication Data

US 2017/0319337 A1    Nov. 9, 2017

Related U.S. Application Data

(62) Division of application No. 14/186,537, filed on Feb. 21, 2014, now Pat. No. 9,744,034.

(60) Provisional application No. 61/777,345, filed on Mar. 12, 2013.

(51) Int. Cl.
*A61F 2/24* (2006.01)

(52) U.S. Cl.
CPC .... *A61F 2/2418* (2013.01); *A61F 2210/0004* (2013.01); *A61F 2220/0075* (2013.01); *A61F 2250/006* (2013.01); *A61F 2250/0039* (2013.01); *A61F 2250/0098* (2013.01)

(58) Field of Classification Search
CPC .... A61F 2/2418; A61F 2/2427–2/2439; A61F 2210/0004; A61F 2220/0075; A61F 2250/0039; A61F 2250/0032; A61F 2250/0085; A61F 2250/0096–2250/0098
See application file for complete search history.

(56) References Cited

U.S. PATENT DOCUMENTS

| | | | |
|---|---|---|---|
| 8,998,981 B2 | 4/2015 | Tuval et al. | |
| 9,149,341 B2 | 10/2015 | Jones et al. | |
| 10,314,701 B2* | 6/2019 | Von Segesser | ....... A61F 2/2418 |
| 2003/0114913 A1 | 6/2003 | Spenser et al. | |
| 2006/0020327 A1* | 1/2006 | Lashinski | ............. A61F 2/2436 623/1.25 |
| 2009/0171432 A1* | 7/2009 | Von Segesser | ....... A61F 2/2427 623/1.11 |
| 2010/0121436 A1* | 5/2010 | Tuval | .................... A61F 2/2418 623/2.17 |

(Continued)

*Primary Examiner* — Paul B Prebilic
(74) *Attorney, Agent, or Firm* — Lerner, David, Littenberg, Krumholz & Mentlik, LLP

(57) ABSTRACT

A prosthetic valve assembly for implantation in a patient's circulatory system includes a stent, a valve member coupled to the stent and defining a preferred landing zone relative to anatomical structures in the patient's circulatory system, and at least one marker positioned in a predetermined relationship relative to the landing zone of the valve member, the marker being visually distinguishable from the stent using an imaging technique. By observing the marker, the prosthetic valve assembly may be implanted in the patient so that certain ones of the anatomical structures lie within the landing zone.

12 Claims, 8 Drawing Sheets

(56) References Cited

U.S. PATENT DOCUMENTS

| | | |
|---|---|---|
| 2010/0172556 A1* | 7/2010 | Cohen .................. A61B 6/5217 |
| | | 382/128 |
| 2010/0198331 A1 | 8/2010 | Rapoza et al. |
| 2010/0249908 A1* | 9/2010 | Chau ..................... A61F 2/2418 |
| | | 623/1.26 |
| 2010/0331972 A1* | 12/2010 | Pintor .................. A61F 2/2409 |
| | | 623/2.11 |
| 2012/0277844 A1 | 11/2012 | Wu |
| 2013/0166023 A1 | 6/2013 | Pipenhagen |
| 2014/0046426 A1 | 2/2014 | Kovalsky |
| 2014/0155990 A1 | 6/2014 | Nyuli et al. |
| 2014/0296706 A1* | 10/2014 | Chronos ............... A61F 2/2496 |
| | | 600/424 |

\* cited by examiner

METHOD OF PLACING A PROSTHETIC VALVE ASSEMBLY IN A PATIENT'S CIRCULATORY SYSTEM

This application is a divisional application of U.S. patent application Ser. No. 14/186,537 filed Feb. 21, 2014, now U.S. Pat. No. 9,744,034 which claims the benefit of the filing date of U.S. Provisional Patent Application No. 61/777,345 filed Mar. 12, 2013, the disclosures of which are hereby incorporated herein by reference.

BACKGROUND OF THE INVENTION

The present disclosure generally relates to devices and methods for facilitating proper placement of a medical prosthesis relative to a patient's anatomical structures. More particularly, the present disclosure relates to a medical prosthesis including markers that facilitate placement of the medical prosthesis relative to the patient's anatomical structures.

Heart failure is defined as the inability of the heart to pump enough blood to sustain normal bodily functions. Heart failure may be associated with a mechanical failure of a native valve. Such failures may arise because of congenital defects or as a result of age-related changes, infections, or other conditions.

Mechanical failures of the heart may result from a valve disorder. The heart has four valves: the tricuspid, pulmonary, mitral, and aortic valves. These valves have tissue flaps that open and close with each heartbeat. The flaps ensure proper blood flow through the four chambers of the heart and to the rest of the body. The heart valves sometimes have the following types of disorders: regurgitation, stenosis, and atresia.

Regurgitation (backflow through or around a valve) often occurs when the valve does not close tightly enough, thereby resulting in blood leaking back into the chambers of the heart rather than flowing forward through the heart or into arteries. Regurgitation often occurs because of prolapse, i.e., when the cusps or leaflets of the valve bulge back into an upper heart chamber during diastole. Stenosis occurs when the cusps or leaflets of a valve stiffen or fuse together, thereby preventing the valve from fully opening and inhibiting sufficient blood flow through the valve. Atresia occurs when a heart valve lacks an opening for blood to pass through.

Heart valve repair or replacement surgery restores or replaces a defective heart valve. The implantation of prosthetic cardiac valves has become increasingly common. One such procedure known as Transcatheter Aortic Valve Implantation (TAVI) uses a prosthetic valve mounted on a stent that displaces the diseased native aortic valve. The prosthetic valve is delivered by compressing it to approximately the width of a pencil and introducing it through a variety of access approaches including a transfemoral, transapical, transaortic, subclavian, or radial approach. Using ultrasound and X-ray guidance, the device is positioned and deployed at the level of the aortic annulus. As the device expands, it is anchored onto and displaces the diseased native valve to restore normal blood flow.

The replacement or repair of the aortic valve with a prosthetic device presents several challenges, including assessing the size and shape of the aortic annulus prior to implantation of the prosthetic device. Selecting an appropriately sized and shaped prosthetic device may pose several challenges because different techniques for measuring the aortic annulus may provide different measurements and measuring during systole or diastole may also have implications for sizing.

Even when an appropriately sized and shaped prosthetic device is selected, precise placement of the device is challenging. Since valves are often made from material that is not radiopaque, such as tissue or fabric, radiologic imaging techniques do not provide a direct way of determining the location of important regions of the valve. The stent typically is metallic and can be visualized in an x-ray image such as a fluoroscopic image. However, even if a clinician possesses a high degree of knowledge as to the construction of the valve assembly, e.g., the placement of the valve with respect to the stent, various regions of the valve assembly may appear to be the same or substantially the same when viewed using radiologic imaging techniques. Due to these challenges, the clinician often finds it difficult to guide the valve to the desired position relative to the patient's vasculature.

Appropriate placement and fit of the valve with respect to a patient's vasculature is important in ensuring proper functioning of the device. An improper fit or placement of the device may result in incomplete apposition or contact with the native aortic annulus, which may cause complications such as perivalvular leakage.

Therefore, a continuing need exists for devices and methods that facilitate the proper placement of prosthetic valves during valve repair or replacement surgery by more accurately and easily determining the location of components of the valve assembly with respect to anatomical landmarks.

BRIEF SUMMARY OF THE INVENTION

Disclosed herein are prosthetic valve assemblies and methods for implanting a prosthetic valve assembly in a patient's circulatory system.

A prosthetic valve assembly for implantation in a patient's circulatory system may include a stent; a valve member coupled to the stent and defining a preferred landing zone relative to anatomical structures in the patient's circulatory system; and at least one marker positioned in a predetermined relationship relative to the landing zone of the valve member, the marker being visually distinguishable from the stent using an imaging technique.

In a method of placing a prosthetic valve assembly in a patient's circulatory system, the prosthetic valve assembly may include a stent, a valve member coupled to the stent, and at least one valve marker positioned in a predetermined relationship to the valve member. The method may include identifying anatomical landmarks in the patient's circulatory system; delivering the prosthetic valve assembly into the patient's circulatory system in the vicinity of the anatomical landmarks; and positioning the prosthetic valve assembly so that the at least one valve marker is in a predetermined position relative to the anatomical landmarks.

These and other embodiments of the present disclosure are more fully described hereinbelow.

BRIEF DESCRIPTION OF THE DRAWINGS

By way of description only, embodiments of the present disclosure are described with reference to the accompanying drawings, in which.

DETAILED DESCRIPTION

Figure 1:
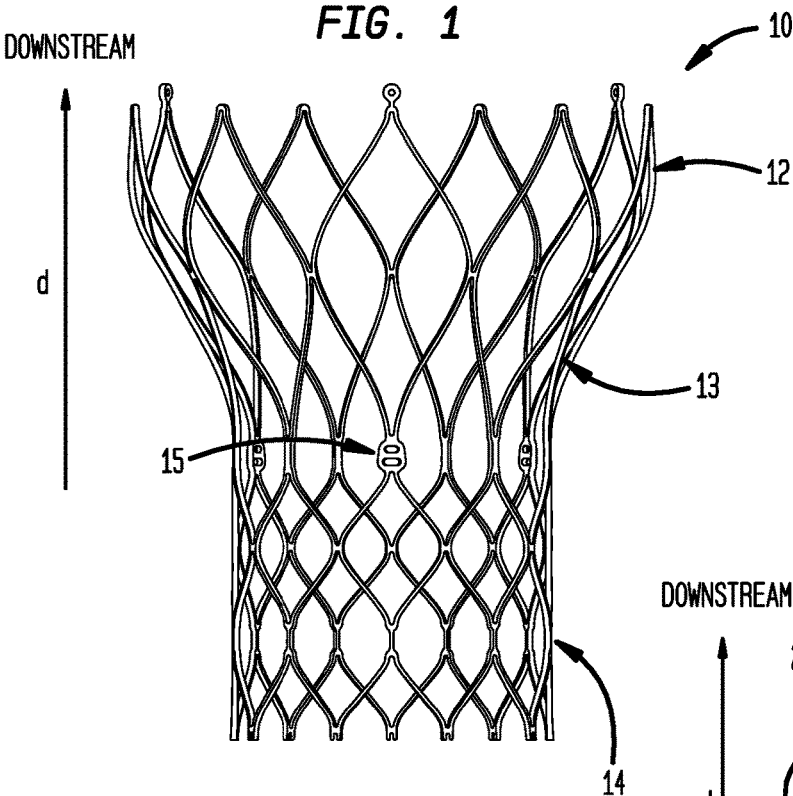
FIG. 1 is an elevational view of a stent.

Particular embodiments of the present disclosure are described with reference to the accompanying drawings. In the figures and in the description that follow, like reference numerals identify similar or identical elements.

A medical prosthesis to which the present invention may be applied is a prosthetic cardiac valve. In the description which follows, the invention will be described in connection with a prosthetic aortic valve, and in particular, a collapsible prosthetic aortic valve. Such collapsible prosthetic valves generally include a plurality of valve leaflets mounted on a collapsible stent. It will be appreciated, however, that the invention is not so limited, and may be applied to other types of collapsible cardiac valves, to noncollapsible cardiac valves, and to other implantable medical devices as appropriate.

FIG. 1 shows a collapsible stent 10 that is transitionable between a collapsed condition for maneuvering to the proper position in the patient and an expanded condition for engagement in the annulus of the patient's aortic valve. Stent 10 includes an aortic section 12, which may be positioned in a patient's aorta, and an annulus section 14, which may be positioned in a patient's aortic annulus. Aortic section 12 is axially spaced from annulus section 14 in a direction referred to herein as the downstream direction d, which is the direction of blood flow through the stent 10 when it is implanted in a patient. A sinus section 13 is disposed between aortic section 12 and annulus section 14. The diameter of annulus section 14 may be substantially uniform and the diameter of aortic section 12 may be substantially uniform. The diameter of stent 10 may increase in the downstream direction d through sinus section 13 such that the diameter of aortic section 12 is larger than the diameter of annulus section 14.

Stent 10 may include commissure attachment features 15 near the downstream end of annulus section 14. A plurality of commissure attachment features 15, e.g., three commissure attachment features, may be equally spaced around the circumference of stent 10. Stent 10 may be self-expandable and may be formed from a shape memory material, such as a nickel titanium alloy (Nitinol). Stent 10 may be formed as a unitary element, e.g., a unitary metallic element. It is to be understood that stents having different configurations than that of stent 10 may be used as appropriate for the particular procedure and the unique anatomy of the patient. For example, during a mitral valve replacement, a stent may be used that does not have aortic or sinus sections.

Figure 2:
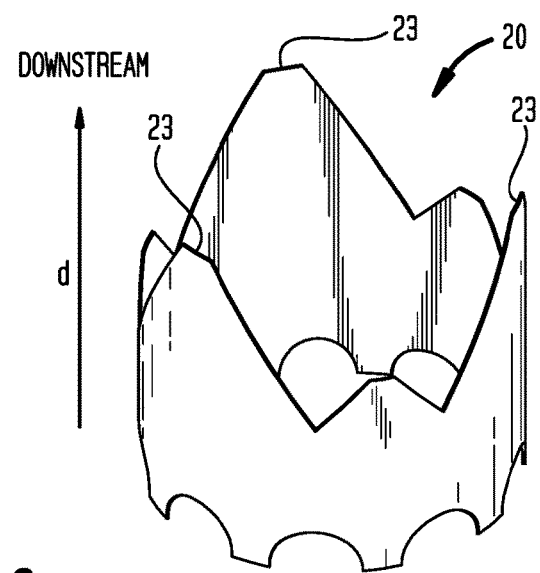
FIG. 2 is a perspective view of a cuff.
Figure 3:
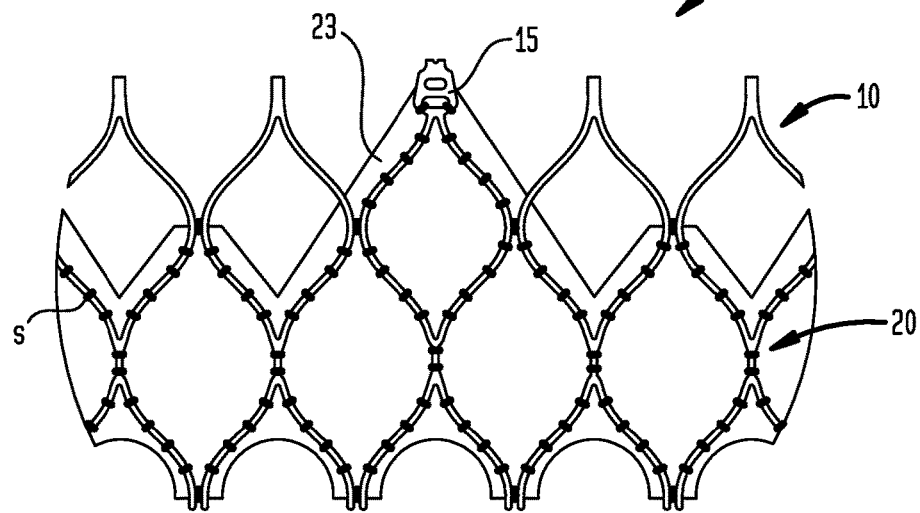
FIG. 3 is a developed view of a portion of a valve subassembly including the stent of FIG. 1 and the cuff of FIG. 2.

FIG. 2 shows a cuff 20 that may be secured to stent 10, preferably in annulus section 14. Cuff 20 may be formed from a natural material, for example, bovine or porcine pericardial tissue, or from a synthetic material, and may be positioned on the inside or outside of annulus section 14 or on both the inside and outside of the annulus section. A valve subassembly 30 including cuff 20 attached to stent 10 is shown in FIG. 3. Cuff 20 may be secured to stent 10 by sutures S or by other techniques known in the art. Enlarged regions 23 of cuff 20 may extend up to commissure attachment features 15 and may be attached to the commissure attachment features.

Figure 4A:
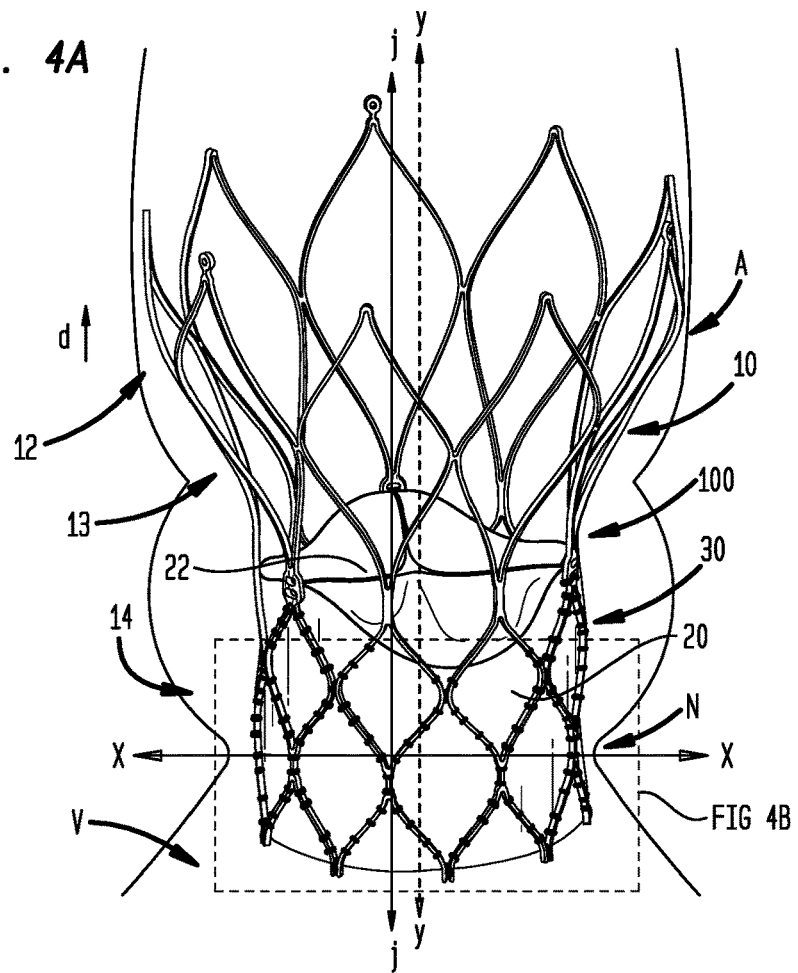
FIG. 4A is a diagrammatic view of a prosthetic valve implanted in place of a patient's aortic valve.

A prosthetic valve 100, shown in FIG. 4A, may include stent 10, with cuff 20 attached to the stent in the annulus section 14 thereof, and a plurality of leaflets 22 secured to the stent and the cuff via suturing or other techniques known in the art. Leaflets 22 and cuff 20 may collectively function as a one-way valve such that blood may flow through valve 100 in one direction but not in the other. Leaflets 22 may be wholly or partly formed of tissue or any suitable polymer. When valve 100 is implanted, leaflets 22 may abut or coapt with one another in diastole such that they cooperate with one another to block the flow of blood in an upstream direction, which is the direction opposite that of downstream direction d.

As a result of the anatomy and acute curvature of the aortic arch, prosthetic valve 100, and particularly leaflets 22, cannot always be aligned with the native valve annulus N. When prosthetic valve 100 is deployed near the native aortic valve, stent 10 and leaflets 22 may be canted toward the descending aorta at the valve annulus N. As a consequence, prosthetic valve leaflets 22 will not be in alignment with the native valve leaflets. The improper positioning of the leaflets 22 with respect to the valve annulus N may adversely affect the functioning of prosthetic heart valve 100. In addition, the orientation of prosthetic heart valve 100 at an oblique angle relative to the plane X-X extending through native valve annulus N may exert uneven forces on surrounding tissue, including the mitral valve annulus, or otherwise interfere with the proper functioning of the mitral valve.

Figure 4B:
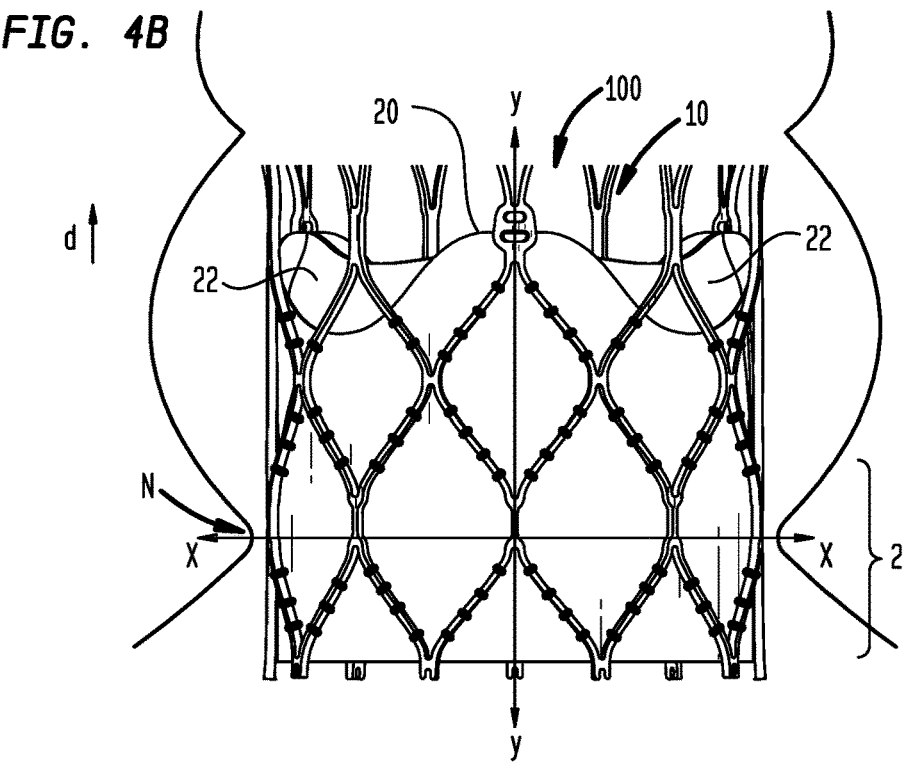
FIG. 4B is a fragmentary view on an enlarged scale of the indicated area of FIG. 4A.
Figure 4C:
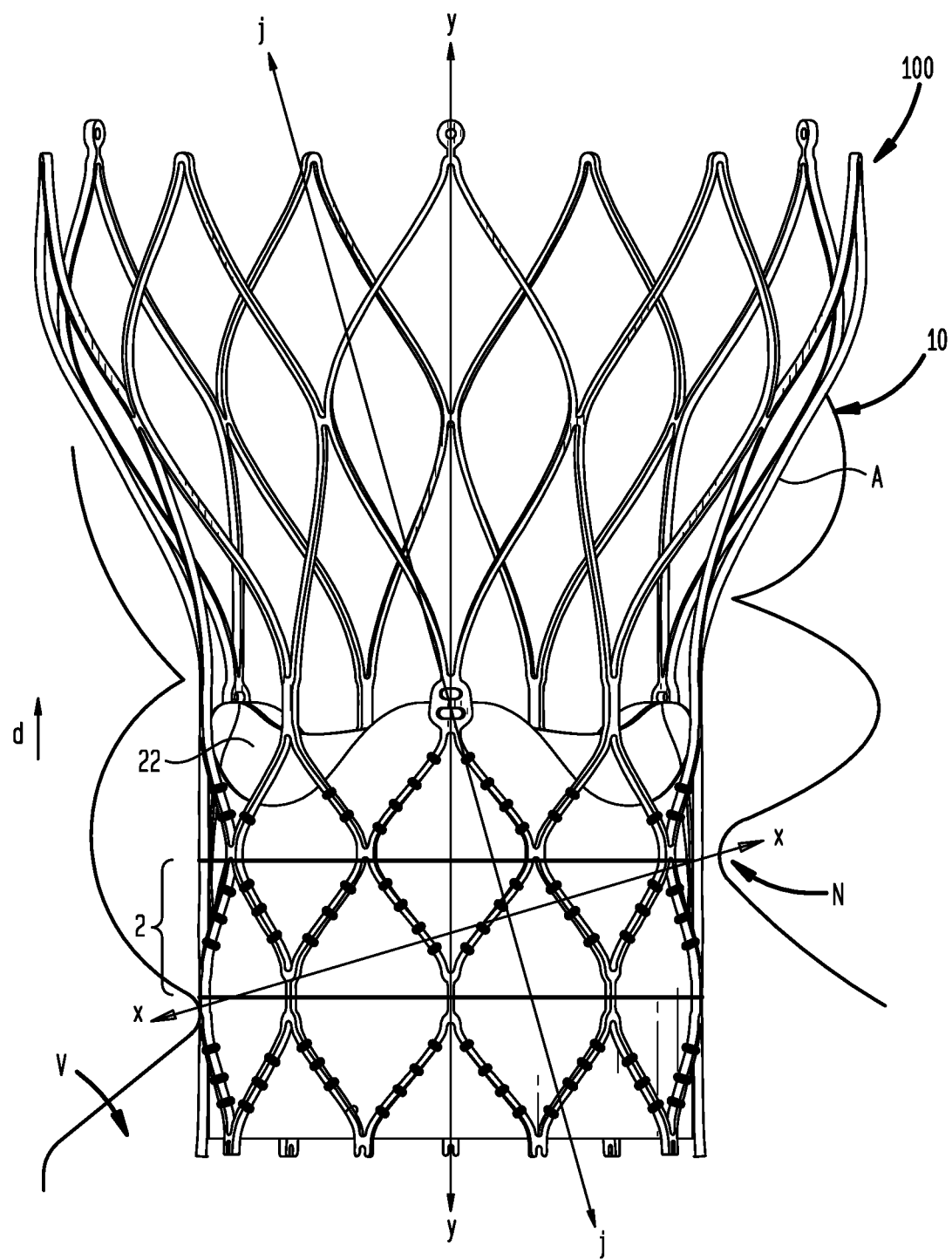
FIG. 4C is a diagrammatic view of the prosthetic valve of FIG. 4A shown relative to another patient's vasculature in which the native aortic annulus is angled relative to the prosthetic valve.

Since the anatomies of patients differ, the size and shape of the aorta will differ from patient to patient. In some patients, as shown in FIG. 4B, the anatomy of aorta A is such that prosthetic valve 100 may be implanted with its longitudinal axis y-y perpendicular to annulus plane X-X. In other patients, as shown in FIG. 4C, the anatomy of the aorta will only allow prosthetic valve 100 to be implanted with its longitudinal axis y-y at an oblique angle to annulus plane X-X. (In FIGS. 4A and 4C, line j-j represents the direction that is perpendicular to the annulus plane X-X.) In either case, it is important to know the location of the plane X-X of native valve annulus N and other anatomical landmarks in order to properly position prosthetic valve 100 relative to the patient's anatomy.

The location of the plane X-X of the patient's native valve annulus may be determined using a variety of imagining modalities including, for example, fluoroscopy, which is an x-ray based radiologic imaging technique used to evaluate moving pulmonary and cardiac structures, and echolocation, which uses sound to evaluate such structures. During fluoroscopy, a contrast medium may be introduced into the circulatory system to facilitate viewing of the patient's soft tissue on the fluoroscope. By identifying three anatomical landmarks, e.g., the lowest point of each of the leaflets of the native valve, annulus plane X-X may be defined and may be used to align with demarcated areas of prosthetic valve 100.

Figure 5:
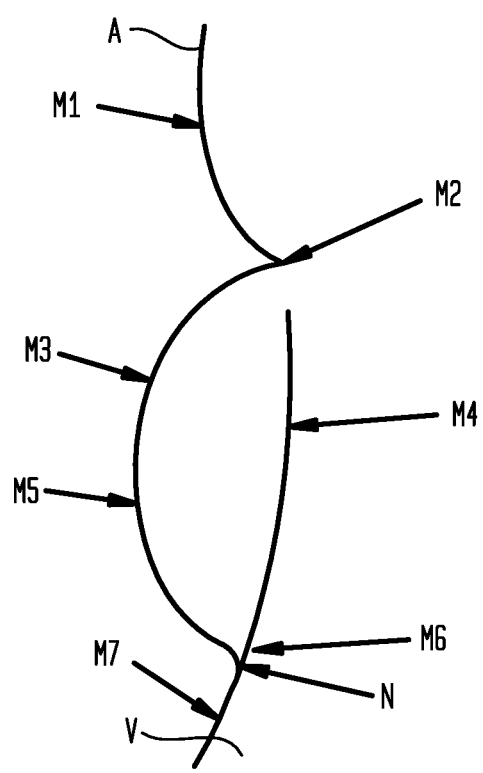
FIG. 5 is a diagrammatic representation showing markers relative to a patient's vasculature.

Referring to FIG. 5, to identify the location, shape, and size of certain target features of the native anatomy, i.e., the target site for positioning the annulus section 14 of prosthetic valve 100 with respect to native annulus N, prior to delivery of the prosthetic heart valve into the patient, markers M1-M7 may be placed in the patient relative to key anatomical landmarks. Markers M1-M7 may be used when the use of contrast to visualize the patient's anatomy is not desired. For example, marker M1 may be placed in aorta A, marker M2 may be placed at the sinotubular junction, marker M3 may be placed at the coronary arteries, marker M4 may be placed at a leaflet, marker M5 may be placed in the sinus of Valsalva, marker M6 may be placed at native annulus N, marker M7 may be placed in the left ventricular outflow tract V, and additional markers may be placed at other key anatomical features and landmarks. A lesser or greater number of markers than described above may be used.

Markers M1-M7 may be radiopaque, i.e., they may block radiation so as to be seen when radiation, such as x-rays, are applied. One example of a radiopaque material from which the markers may be formed is tungsten. Markers M1-M7 may have special characteristics, including but not limited to, bio-absorbability, permanency, or a drug eluting and/or radiation emitting capability. The markers may have any one of these characteristics or any combination of same. Families of bioabsorbable polymers from which the markers may be formed include polyesters, poly(amino acids), polyanhydrides, polyorthoesters, polyurethanes, polycarbonates, homopolymers and copolymers of poly(lactic acid), poly(glycolic acid), copolyesters of e-caprolactone, trimethylene carbonate, and para-doxianone. Markers M1-M7 may be formed from a bioabsorbable material that is also radiopaque. For example, markers M1-M7 may be formed from a bioabsorbable polymer mixed with a radiopaque material, for example, tungsten powder. Markers M1-M7 may be arranged to define a plane, which the surgeon or technician may use to assure proper positioning of prosthetic valve 100 relative to various anatomical structures. Markers M1-M7 may have a radiopacity differing from the radiopacity of the stent.

Prosthetic valve 100 may be delivered to an implantation site using one of a variety of different techniques. For example, valve 100 may be delivered through a patient's vasculature using a transfemoral or other intravascular approach, may be delivered directly through the heart muscle such as in a transapical approach, or may be delivered and implanted using open heart surgical techniques, and/or sutureless valve repair techniques. The implantation of prosthetic valve 100 relative to the patient's vasculature is described below with further reference to FIGS. 4A-4C.

Figure 6A:
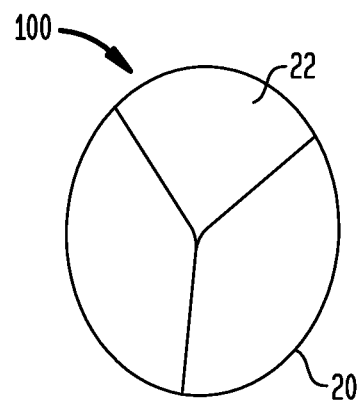
FIG. 6A is a top view of the leaflets of the prosthetic valve of FIG. 4A shown in a first state.
Figure 6B:
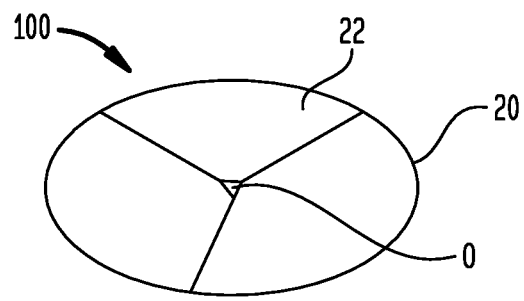
FIG. 6B is a top view of the leaflets of the prosthetic valve of FIG. 4A shown in a second state.

Preferably, prosthetic valve 100 is implanted in native valve annulus N so that the annulus section 14 thereof is positioned at plane X-X. In such position, plane X-X will extend through the cuff 20 secured in annulus section 14 of stent 10. When prosthetic valve 100 is implanted in native valve annulus N, it may be held in place therein primarily by outward radial forces exerted by stent 10 on the native valve annulus. Positioning annulus section 14, and hence cuff 20, in native valve annulus N facilitates sealing, anchoring, and proper functioning of prosthetic valve 100. In that regard, prosthetic valve 100 may be implanted with its longitudinal axis y-y perpendicular to plane X-X (FIG. 4A) or at an oblique angle to plane X-X (FIG. 4C). Positioning prosthetic valve 100 so that its longitudinal axis y-y is perpendicular to plane X-X is preferred so that leaflets 22 are aligned with the native valve leaflets and stent 10 more evenly applies forces to the surrounding tissue. Such positioning facilitates coaptation of leaflets 22 (FIG. 6A) and sealing at the interface between the prosthetic valve and native valve annulus N. When prosthetic valve 100 is not properly positioned, leaflets 22 may not fully coapt, resulting in an opening O where the leaflets would otherwise meet (FIG. 6B) and higher stresses where the leaflets are joined to stent 10.

Stated another way, prosthetic valve 100 has a preferred landing zone 2 (FIG. 7A), which includes an area of annulus section 14 within which native valve annulus N preferably lies when the valve is properly implanted. By positioning the landing zone 2 of prosthetic valve 100 with respect to anatomical features, such as annulus plane X-X, perivalvular leakage and regurgitation may be minimized Proper positioning of landing zone 2 with respect to native valve annulus N may facilitate the proper protrusion of prosthetic valve 100 into the left ventricle, as well as sealing at the interface of stent 10 and cuff 20 with the surrounding tissue.

Figure 7A:
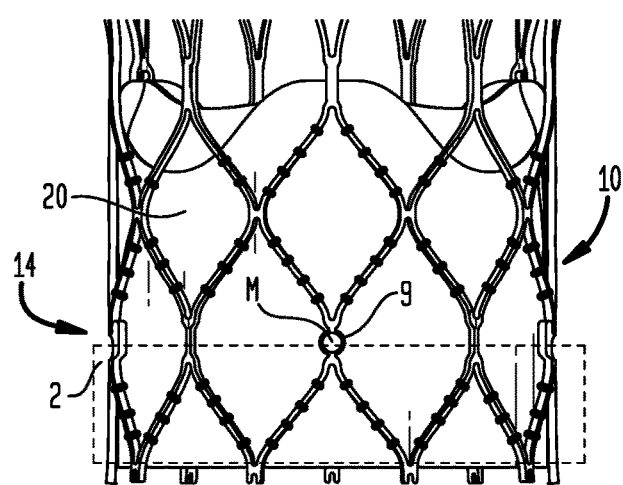
FIG. 7A is a fragmentary elevational view of a portion of the prosthetic valve of FIG. 4A in conjunction with a marker.
Figure 7B:
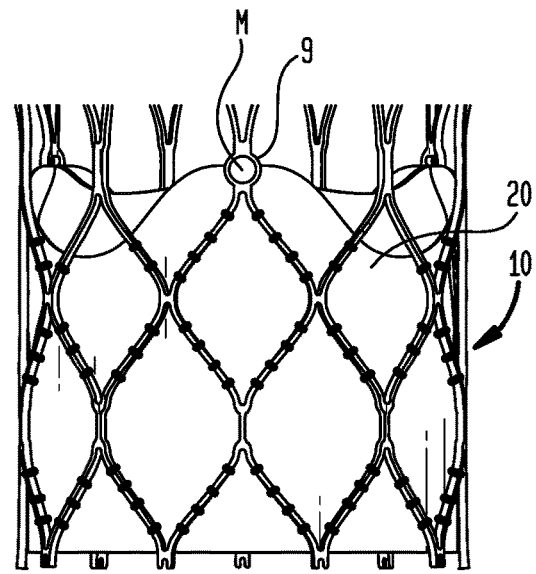
FIG. 7B is a fragmentary elevational view of a portion of the prosthetic valve of FIG. 4A in conjunction with another marker.

Additional markers M may be operatively coupled to stent 10 to assist in positioning prosthetic valve 100 with respect to the patient's native valve or a previously implanted prosthetic valve. Markers M may be formed from a radiopaque material so as to be visible using various techniques for imaging within the patient's body. As shown in FIGS. 7A-7B, stent 10 may include apertures or receptacles 9 at predetermined positions relative to cuff 20. Markers M may be secured within these receptacles 9. During the implantation of prosthetic valve 100, markers M may provide an indication of the position of cuff 20, such as the location at which cuff 20 is secured to stent 10.

Figure 8A:
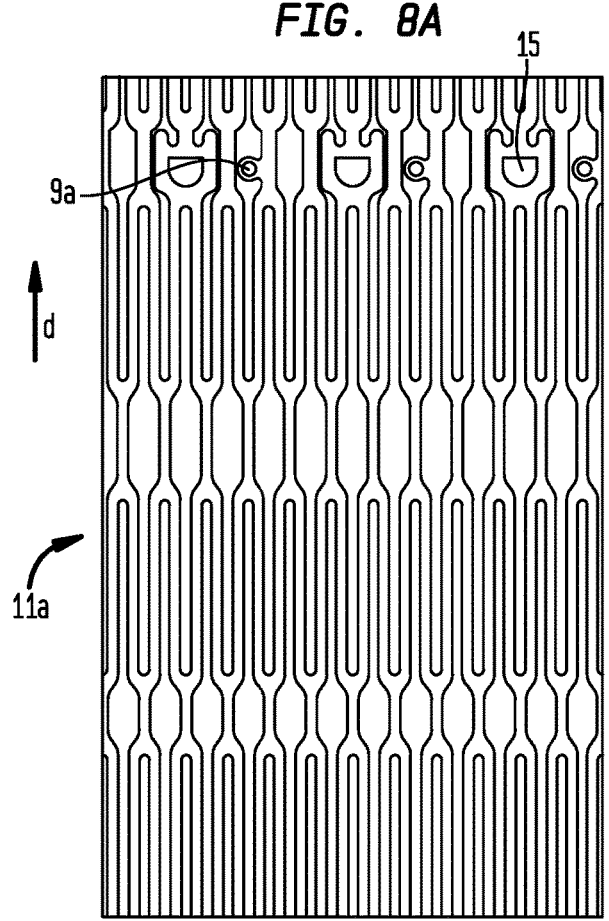
FIG. 8A is a developed view of a portion of a stent including receptacles.
Figure 8B:
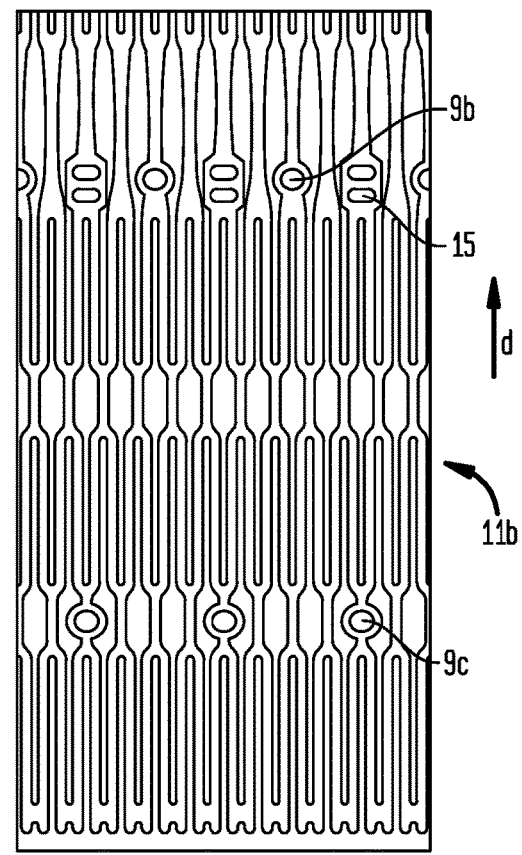
FIG. 8B is a developed view of a portion of another stent including receptacles.

Referring to FIG. 8A, receptacles 9a may be spaced about the circumference of a stent 11a in circumferential alignment with commissure attachment features 15. Such positioning will enable the user to assure that the prosthetic valve is positioned so that the leaflets thereof do not interfere with the coronary ostia. Alternatively, receptacles 9 may be positioned closer to the free end of the annulus section of the prosthetic valve. Such positioning will enable the user to assure that the end of the prosthetic valve does not protrude too far into the left ventricle. In the embodiment of FIG. 8B, stent 11b includes a first set of receptacles 9b in circumferential alignment with commissure attachment features 15, and a second set of receptacles 9c spaced around the circumference of the stent at an axial position closer to the free end of the annulus section. A marker M may be coupled to each one of receptacles 9a-c. Markers M may be placed around the circumference of the stent in substantially the same axial position relative to the longitudinal axis of the stent such that these markers will define a plane in a predetermined location relative to landing zone 2. Additional markers M may be operatively coupled to the stent to further delineate the boundaries of landing zone 2, that is, the upper and lower edges of the landing zone.

Markers M may define a plane at a predetermined location relative to landing zone 2. During implantation of prosthetic valve 100, the plane relative to landing zone 2 may be positioned relative to a plane corresponding to various anatomical structures, such as annulus plane X-X.

Receptacles 9a-c may facilitate the placement of additional features with respect to the stent and may provide a tactile and/or mechanical means of determining positioning relative to certain regions of the stent. For example, receptacles 9a-c may be located by feel or tactiley or may include magnets (not shown) that interact with other magnets or ferrous materials on the devices or tools being introduced into the site.

Figure 8C:
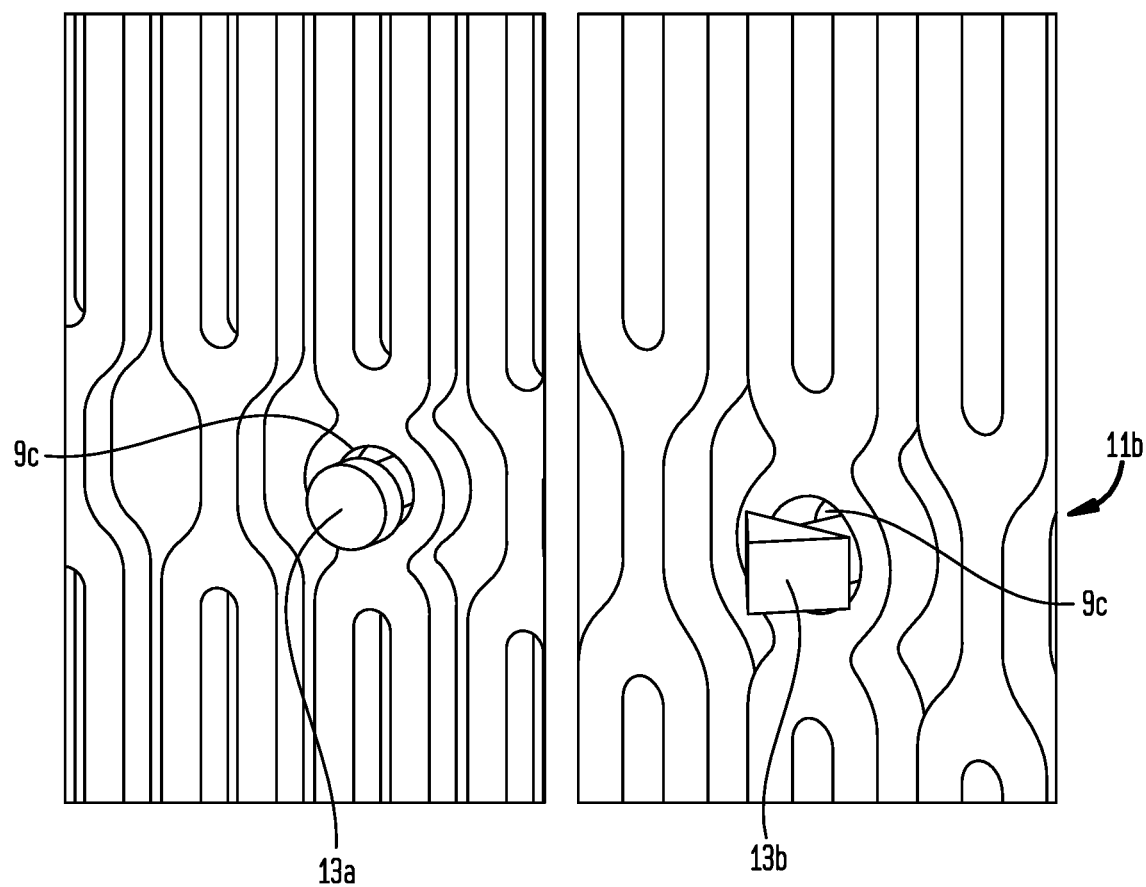
FIG. 8C is an enlarged perspective view of a portion of a stent having locating features of a valve disposed within receptacles of the stent.

Receptacles 9a-c may facilitate a valve-in-valve replacement and/or may receive the sutures or underwires used to secure elements such as cuff 20 and/or leaflets 22 to the stent. For example, as shown in FIG. 8C, receptacles 9a-c may receive locating features 13a, 13b which may be operatively coupled to a device to be coupled to the stent. In one arrangement, during a valve-in-valve replacement procedure, a replacement stent (not shown) may include the locating features 13a, 13b to assure that the replacement stent is aligned substantially in the same position and orientation with respect to certain anatomical structures as the previously implanted stent, thereby facilitating proper placement of the replacement valve with respect to the native valve. In another arrangement, receptacles 9a-c and locating features 13a, 13b may be magnetically coupleable, which may facilitate guiding the locating features toward the receptacles for attachment of the device to be connected to the stent. Locating features 13a, 13b may be radiopaque and may be differently shaped such that they are readily distinguishable from one another. Locating features 13a, 13b may be releasably secured to the receptacles.

Figure 9:
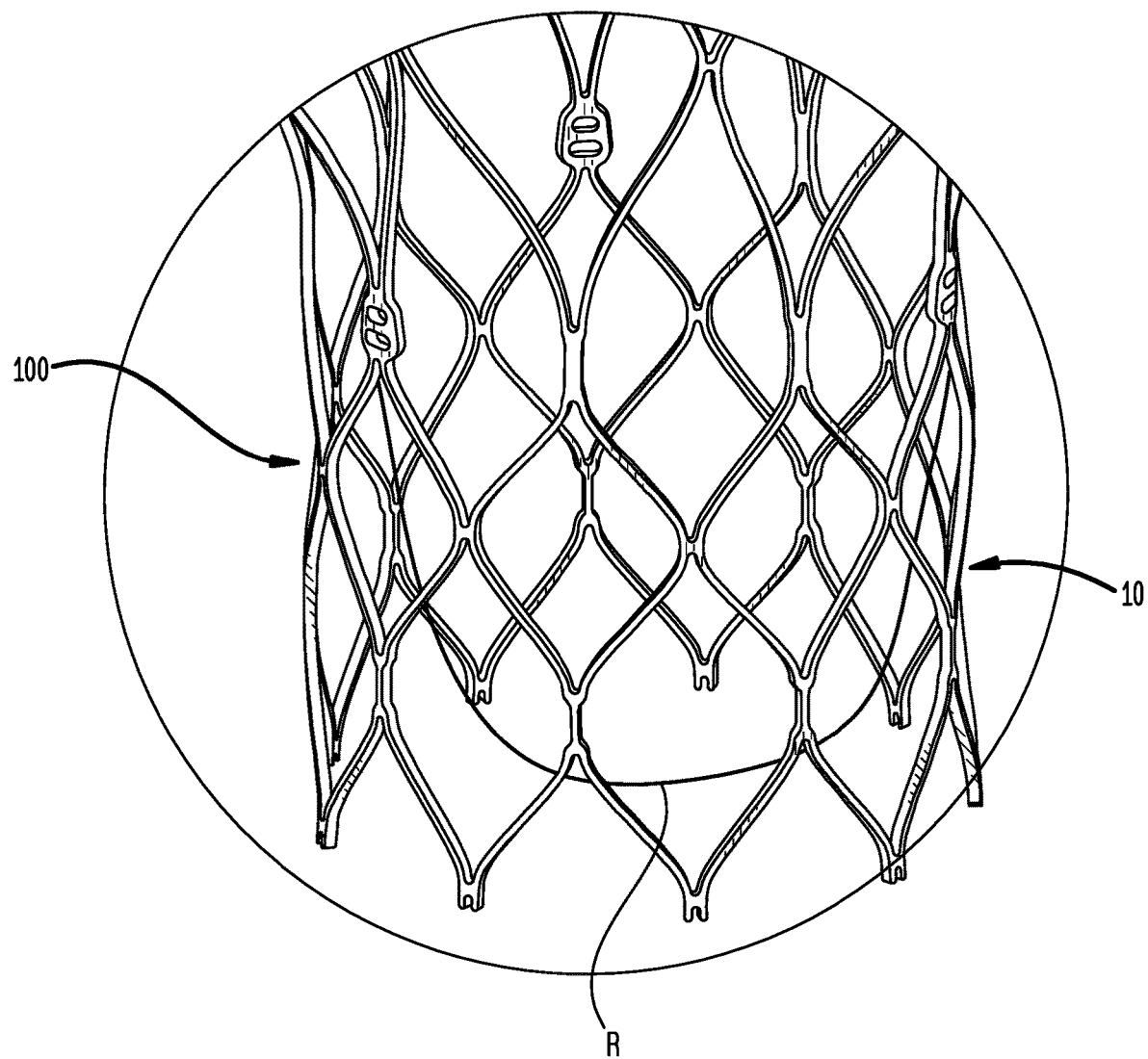
FIG. 9 is an enlarged fragmentary view of a prosthetic valve including a radiopaque suture disposed along a contour of the valve.

FIG. 9 is an enlarged fragmentary view of a prosthetic valve depicting a radiopaque suture R that is disposed along a contour of the valve to facilitate viewing of the outline of at least a portion of the valve using radiologic imaging techniques. The radiopaque suture may be disposed along the contour of the leaflet belly of the valve, and may join leaflets 22 to cuff 20. Radiopaque suture R may facilitate viewing of otherwise non-radiopaque components of a prosthetic valve, such as components formed from tissue. Radiopaque suture R may be used in conjunction with or as alternative to markers M shown in FIGS. 7A-7B.

Cuff 20 may be impregnated with substances that are readily visualized using radiologic imaging techniques, such as iodine or silver-based solutions. Alternatively, markers may be operatively coupled to or embedded within cuff 20 at particular locations of prosthetic valve 100, for example, at or near the commissures of leaflets 22.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the present claims. For example, although the present disclosure describes devices and methods for implanting a prosthetic cardiac valve in a native valve annulus, it is to be understood that aspects of the present disclosure may be applied to the implantation of prosthetic devices in other body lumens. Moreover, although stent 10 is described with reference to aortic valve repair, it is to be understood that the stent may be used to repair or replace other valves, such as the mitral valve. Also, for example, although markers are described as being placed on collapsible prosthetic valves, such markers may be placed on other devices as well, including surgical valves or other medical implants in order to facilitate the proper positioning and orientation of the implant on insertion into a patient. For example, such markers may be placed on a polymeric stent post supporting tissue portions of a surgical valve.

The above-described embodiments and variations of the invention can be combined in ways other than as specifically described above. It is intended to cover all such variations which lie within the scope and spirit of the invention.

To summarize the foregoing description, a prosthetic valve assembly for implantation in a patient's circulatory system may include a stent; a valve member coupled to the stent and defining a preferred landing zone relative to anatomical structures in the patient's circulatory system; and at least one marker positioned in a predetermined relationship to the landing zone of the valve member, the marker being visually distinguishable from the stent using an imaging technique; and/or the marker may be operatively coupled to one of the stent or the valve member; and/or the landing zone may have a first boundary and a second boundary, and the marker may identify the first and second boundaries of the landing zone; and/or the marker may include three markers defining a plane having a fixed position relative to the landing zone; and/or the marker may include a radiopaque suture connected to the valve member; and/or the marker may be formed from a radiopaque material; and/or the marker may have a greater radiopacity than that of the stent; and/or the marker may have a predetermined geometric shape; and/or the marker may include a plurality of markers each having a predetermined geometric shape, the shape of one of the markers being different from the shape of another of the markers; and/or the marker may be formed from a bioabsorbable material.

Also described was a method of placing a prosthetic valve assembly in a patient's circulatory system, the prosthetic valve assembly including a stent, a valve member coupled to the stent, and at least one valve marker positioned in a predetermined relationship to the valve member. The method may include identifying anatomical landmarks in the patient's circulatory system; delivering the prosthetic valve assembly into the patient's circulatory system in the vicinity of the anatomical landmarks; and positioning the prosthetic valve assembly so that the at least one valve marker is in a predetermined position relative to the anatomical landmarks; and/or the at least one valve member may be radiopaque; and/or the anatomical landmarks may define a first plane, and the prosthetic valve assembly may include a plurality of valve markers defining a landing zone, the positioning step including positioning the prosthetic valve assembly so that the first plane lies in the landing zone; and/or the anatomical landmarks may define a first plane and the prosthetic valve assembly may include a plurality of valve markers defining a second plane, the positioning step including positioning the prosthetic valve assembly so that the second plane is at a desired position relative to the first plane; and/or the positioning step may include positioning the prosthetic valve assembly so that the second plane is at a desired orientation relative to the first plane; and/or the first plane may extend through a native valve annulus, and the positioning step may include positioning the prosthetic valve assembly so that the second plane is aligned with the native valve annulus; and/or the identifying step may include placing a plurality of anatomical markers in the patient's circulatory system at fixed positions relative to the anatomical landmarks; and/or the plurality of anatomical markers may be radiopaque.

The invention claimed is:

1. A method of placing a prosthetic valve assembly in a patient's circulatory system, the prosthetic valve assembly having an expanded condition and a collapsed condition and including a metallic stent having an inlet end, an annulus section adjacent the inlet end, an outlet end, an aortic section adjacent the outlet end and a plurality of commissure features at a spaced distance from both the inlet end and the outlet end, the metallic stent including the commissure features being formed from a first material, a valve member coupled to the stent so as to define on the stent a preferred landing zone in the annulus section between the inlet end of the stent and the commissure features, and a plurality of valve markers formed from a second material different from the first material and positioned on the stent at predetermined positions relative to the landing zone, the valve markers identifying a first boundary of the landing zone in the annulus section and closer to the inlet end of the stent and a second boundary of the landing zone in the annulus section and closer to the outlet end of the stent, the method comprising:

identifying anatomical landmarks in the patient's circulatory system, the anatomical landmarks defining a first plane;

placing a plurality of anatomical markers in the patient's circulatory system at fixed positions relative to the anatomical landmarks;

delivering the prosthetic valve assembly into the patient's circulatory system in the vicinity of the anatomical markers; and positioning the prosthetic valve assembly so that the first plane lies in the annulus section of the stent between the first boundary of the landing zone and the second boundary of the landing zone.

2. A method of placing a prosthetic valve assembly in a patient's circulatory system, the prosthetic valve assembly having an expanded condition and a collapsed condition and including a metallic stent extending in a longitudinal direction between an inlet end and an outlet end and having a plurality of commissure features at a spaced distance from both the inlet end and the outlet end, a valve member coupled to the stent, and a plurality of valve markers positioned on the stent so as to define a first plane orthogonal to the longitudinal direction, the method comprising:

placing a plurality of anatomical markers in the patient's circulatory system at fixed positions relative to anatomical landmarks in the patient's circulatory system;

identifying the anatomical landmarks in the patient's circulatory system based on the anatomical markers, the anatomical landmarks defining a second plane;

delivering the prosthetic valve assembly into the patient's circulatory system in the vicinity of the anatomical landmarks; and positioning the prosthetic valve assembly so that the first plane is at a desired position relative to the second plane.

3. The method as claimed in claim 1, wherein the plurality of valve markers are radiopaque.

4. The method as claimed in claim 2, wherein the plurality of valve markers are radiopaque.

5. The method as claimed in claim 2, wherein the positioning step includes changing the angle of the prosthetic valve assembly so that the first plane is at a desired angular orientation relative to the second plane.

6. The method as claimed in claim 5, wherein the second plane extends through a native valve annulus, and the positioning step includes positioning the prosthetic valve assembly so that the first plane is aligned with the native valve annulus.

7. The method as claimed in claim 1, wherein the plurality of anatomical markers are radiopaque.

8. The method as claimed in claim 2, wherein the plurality of anatomical markers are radiopaque.

9. The method as claimed in claim 1, wherein the first plane extends through a native valve annulus, and the positioning step includes positioning the prosthetic valve assembly so that the native valve annulus lies in the landing zone.

10. The method as claimed in claim 1, wherein the annulus section has a first diameter and the aortic section has a second diameter, the second diameter being larger than the first diameter.

11. The method as claimed in claim 1, wherein the metallic stent has a unitary construction.

12. The method as claimed in claim 1, wherein the valve member includes a plurality of leaflets spaced from the outlet end of the stent.

* * * * *